(12) United States Patent
Bokil

(10) Patent No.: US 9,037,256 B2
(45) Date of Patent: May 19, 2015

(54) METHODS AND SYSTEM FOR TARGETED BRAIN STIMULATION USING ELECTRICAL PARAMETER MAPS

(75) Inventor: Hemant Sharad Bokil, Cambridge, MA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 386 days.

(21) Appl. No.: 13/600,855

(22) Filed: Aug. 31, 2012

(65) Prior Publication Data

US 2013/0060305 A1 Mar. 7, 2013

Related U.S. Application Data

(60) Provisional application No. 61/530,142, filed on Sep. 1, 2011.

(51) Int. Cl.
*A61N 1/00* (2006.01)
*A61N 1/36* (2006.01)
*A61N 1/05* (2006.01)

(52) U.S. Cl.
CPC .......... *A61N 1/36146* (2013.01); *A61N 1/0529* (2013.01); *A61N 1/0551* (2013.01)

(58) Field of Classification Search
USPC ...................................... 607/45, 62
See application file for complete search history.

(56) References Cited

U.S. PATENT DOCUMENTS

| | | |
|---|---|---|
| 5,099,846 A | 3/1992 | Hardy |
| 5,361,763 A | 11/1994 | Kao et al. |
| 5,452,407 A | 9/1995 | Crook |
| 5,724,985 A | 3/1998 | Snell et al. |
| 5,782,762 A | 7/1998 | Vining |
| 5,938,688 A | 8/1999 | Schiff |
| 6,066,163 A | 5/2000 | John |
| 6,083,162 A | 7/2000 | Vining |
| 6,106,460 A | 8/2000 | Panescu et al. |
| 6,240,308 B1 | 5/2001 | Hardy et al. |
| 6,289,239 B1 | 9/2001 | Panescu et al. |
| 6,310,619 B1 | 10/2001 | Rice |
| 6,319,241 B1 | 11/2001 | King et al. |
| 6,351,675 B1 | 2/2002 | Tholen et al. |

(Continued)

FOREIGN PATENT DOCUMENTS

| | | |
|---|---|---|
| WO | 01/90876 A1 | 11/2001 |
| WO | 2004/019799 A2 | 3/2004 |

(Continued)

OTHER PUBLICATIONS

Butson et al., "StimExplorer: Deep Brain Stimulation Parameter Selection Software System," Acta Neurochirugica, Jan. 1, 2007, vol. 97, No. 2, pp. 569-574.

(Continued)

*Primary Examiner* — Nicole F Lavert
(74) *Attorney, Agent, or Firm* — Lowe Graham Jones PLLC; Bruce E. Black

(57) ABSTRACT

A system and method for selecting optimal stimulation parameter settings for a therapeutic neural stimulation for a current patient may include obtaining, by at least one processor, electrical parameter maps and corresponding score values of a patient population, and processing, by the at least one processor, the parameter maps and the score values to evaluate, based on a set of score criteria, parameter maps associated with potential stimulation parameter settings.

28 Claims, 9 Drawing Sheets

(56) References Cited

U.S. PATENT DOCUMENTS

| | | |
|---|---|---|
| 6,389,311 B1 | 5/2002 | Whayne et al. |
| 6,463,328 B1 | 10/2002 | John |
| 6,491,699 B1 | 12/2002 | Henderson et al. |
| 6,539,263 B1 | 3/2003 | Schiff et al. |
| 6,622,048 B1 | 9/2003 | Mann et al. |
| 6,690,972 B2 | 2/2004 | Conley et al. |
| 6,694,162 B2 | 2/2004 | Hartlep |
| 6,694,163 B1 | 2/2004 | Vining |
| 6,748,098 B1 | 6/2004 | Rosenfeld |
| 6,788,969 B2 | 9/2004 | Dupree et al. |
| 6,795,737 B2 | 9/2004 | Gielen et al. |
| 6,827,681 B2 | 12/2004 | Tanner et al. |
| 6,830,544 B2 | 12/2004 | Tanner |
| 6,909,913 B2 | 6/2005 | Vining |
| 7,003,349 B1 | 2/2006 | Andersson et al. |
| 7,003,352 B1 | 2/2006 | Whitehurst |
| 7,008,370 B2 | 3/2006 | Tanner et al. |
| 7,035,690 B2 | 4/2006 | Goetz |
| 7,043,293 B1 | 5/2006 | Baura |
| 7,050,857 B2 | 5/2006 | Samuelsson et al. |
| 7,107,102 B2 | 9/2006 | Daignault, Jr. et al. |
| 7,136,518 B2 | 11/2006 | Griffin et al. |
| 7,136,695 B2 | 11/2006 | Pless et al. |
| 7,146,219 B2 | 12/2006 | Sieracki et al. |
| 7,146,223 B1 | 12/2006 | King |
| 7,151,961 B1 | 12/2006 | Whitehurst et al. |
| 7,155,279 B2 | 12/2006 | Whitehurst et al. |
| 7,167,760 B2 | 1/2007 | Dawant et al. |
| 7,177,674 B2 | 2/2007 | Echauz et al. |
| 7,181,286 B2 | 2/2007 | Sieracki et al. |
| 7,184,837 B2 | 2/2007 | Goetz |
| 7,209,787 B2 | 4/2007 | DiLorenzo |
| 7,216,000 B2 | 5/2007 | Sieracki et al. |
| 7,217,276 B2 | 5/2007 | Henderson et al. |
| 7,218,968 B2 | 5/2007 | Condie et al. |
| 7,231,254 B2 | 6/2007 | DiLorenzo |
| 7,239,910 B2 | 7/2007 | Tanner |
| 7,239,926 B2 | 7/2007 | Goetz |
| 7,242,984 B2 | 7/2007 | DiLorenzo |
| 7,252,090 B2 | 8/2007 | Goetz |
| 7,254,446 B1 | 8/2007 | Erickson et al. |
| 7,257,447 B2 | 8/2007 | Cates et al. |
| 7,266,412 B2 | 9/2007 | Stypulkowski |
| 7,295,876 B1 | 11/2007 | Erickson |
| 7,313,430 B2 | 12/2007 | Urquhart et al. |
| 7,324,851 B1 | 1/2008 | DiLorenzo |
| 7,346,382 B2 | 3/2008 | McIntyre et al. |
| 7,388,974 B2 | 6/2008 | Yanagita |
| 7,463,928 B2 | 12/2008 | Lee et al. |
| 7,499,048 B2 | 3/2009 | Sieracki et al. |
| 7,505,815 B2 | 3/2009 | Lee et al. |
| 7,548,786 B2 | 6/2009 | Lee et al. |
| 7,603,177 B2 | 10/2009 | Sieracki et al. |
| 7,617,002 B2 | 11/2009 | Goetz |
| 7,623,918 B2 | 11/2009 | Goetz |
| 7,657,319 B2 | 2/2010 | Goetz et al. |
| 7,676,273 B2 | 3/2010 | Goetz et al. |
| 7,826,902 B2 | 11/2010 | Stone et al. |
| 7,848,802 B2 | 12/2010 | Goetz et al. |
| 2004/0034394 A1 | 2/2004 | Woods et al. |
| 2004/0044279 A1 | 3/2004 | Lewin et al. |
| 2004/0106916 A1 | 6/2004 | Quaid et al. |
| 2004/0199216 A1 | 10/2004 | Lee et al. |
| 2004/0267330 A1 | 12/2004 | Lee et al. |
| 2005/0060001 A1 | 3/2005 | Singhal et al. |
| 2005/0060009 A1 | 3/2005 | Goetz |
| 2005/0070781 A1 | 3/2005 | Dawant et al. |
| 2005/0171587 A1 | 8/2005 | Daglow et al. |
| 2006/0017749 A1 | 1/2006 | McIntyre et al. |
| 2006/0020292 A1 | 1/2006 | Goetz et al. |
| 2006/0094951 A1 | 5/2006 | Dean et al. |
| 2006/0235472 A1 | 10/2006 | Goetz et al. |
| 2006/0259079 A1 | 11/2006 | King |
| 2007/0017749 A1 | 1/2007 | Dold et al. |
| 2007/0043268 A1 | 2/2007 | Russell |
| 2007/0049817 A1 | 3/2007 | Preiss et al. |
| 2007/0083104 A1 | 4/2007 | Butson et al. |
| 2007/0123953 A1 | 5/2007 | Lee et al. |
| 2007/0129769 A1 | 6/2007 | Bourget et al. |
| 2007/0156186 A1 | 7/2007 | Lee et al. |
| 2007/0162086 A1 | 7/2007 | DiLorenzo |
| 2007/0185544 A1 | 8/2007 | Dawant et al. |
| 2007/0191912 A1 | 8/2007 | Fischer et al. |
| 2007/0203450 A1 | 8/2007 | Berry |
| 2007/0203538 A1 | 8/2007 | Stone et al. |
| 2007/0203539 A1 | 8/2007 | Stone et al. |
| 2007/0203540 A1 | 8/2007 | Goetz et al. |
| 2007/0203541 A1 | 8/2007 | Goetz et al. |
| 2007/0203543 A1 | 8/2007 | Stone et al. |
| 2007/0203544 A1 | 8/2007 | Goetz et al. |
| 2007/0203545 A1 | 8/2007 | Stone et al. |
| 2007/0203546 A1 | 8/2007 | Stone et al. |
| 2007/0213789 A1 | 9/2007 | Nolan et al. |
| 2007/0213790 A1 | 9/2007 | Nolan et al. |
| 2007/0244519 A1 | 10/2007 | Keacher et al. |
| 2007/0245318 A1 | 10/2007 | Goetz et al. |
| 2007/0255321 A1 | 11/2007 | Gerber et al. |
| 2007/0255322 A1 | 11/2007 | Gerber et al. |
| 2007/0276441 A1 | 11/2007 | Goetz |
| 2007/0282189 A1 | 12/2007 | Dan et al. |
| 2007/0288064 A1 | 12/2007 | Butson et al. |
| 2008/0027514 A1 | 1/2008 | DeMulling et al. |
| 2008/0071150 A1 | 3/2008 | Miesel et al. |
| 2008/0081982 A1 | 4/2008 | Simon et al. |
| 2008/0103533 A1 | 5/2008 | Patel et al. |
| 2008/0123922 A1 | 5/2008 | Gielen et al. |
| 2008/0141217 A1 | 6/2008 | Goetz et al. |
| 2008/0154340 A1 | 6/2008 | Goetz et al. |
| 2008/0163097 A1 | 7/2008 | Goetz et al. |
| 2008/0183256 A1 | 7/2008 | Keacher |
| 2008/0215118 A1 | 9/2008 | Goetz et al. |
| 2008/0269588 A1 | 10/2008 | Csavoy et al. |
| 2008/0300654 A1 | 12/2008 | Lambert et al. |
| 2009/0082640 A1 | 3/2009 | Kovach et al. |
| 2009/0082829 A1 | 3/2009 | Panken et al. |
| 2009/0112289 A1 | 4/2009 | Lee et al. |
| 2009/0149917 A1 | 6/2009 | Whitehurst et al. |
| 2009/0196471 A1 | 8/2009 | Goetz et al. |
| 2009/0196472 A1 | 8/2009 | Goetz et al. |
| 2009/0198306 A1* | 8/2009 | Goetz et al. ............... 607/59 |
| 2009/0204192 A1 | 8/2009 | Carlton et al. |
| 2009/0276008 A1 | 11/2009 | Lee et al. |
| 2009/0281595 A1 | 11/2009 | King et al. |
| 2009/0281596 A1 | 11/2009 | King et al. |
| 2009/0287271 A1 | 11/2009 | Blum et al. |
| 2009/0287272 A1 | 11/2009 | Kokones et al. |
| 2009/0287273 A1 | 11/2009 | Carlton et al. |
| 2009/0287467 A1 | 11/2009 | Sparks et al. |
| 2009/0299164 A1 | 12/2009 | Singhal et al. |
| 2009/0299165 A1 | 12/2009 | Singhal et al. |
| 2009/0299380 A1 | 12/2009 | Singhal et al. |
| 2010/0010646 A1 | 1/2010 | Drew et al. |
| 2010/0023130 A1 | 1/2010 | Henry et al. |
| 2010/0049276 A1 | 2/2010 | Blum et al. |
| 2010/0049280 A1 | 2/2010 | Goetz |
| 2011/0191275 A1 | 8/2011 | Lujan et al. |

FOREIGN PATENT DOCUMENTS

| | | |
|---|---|---|
| WO | 2007/097859 A1 | 8/2007 |
| WO | 2007/097861 A1 | 8/2007 |
| WO | 2007/100427 A1 | 9/2007 |
| WO | 2007/100428 A1 | 9/2007 |
| WO | 2007/112061 A2 | 10/2007 |
| WO | 2010/120823 A2 | 10/2010 |
| WO | 2011/139779 A1 | 11/2011 |
| WO | 2011/159688 A2 | 12/2011 |

OTHER PUBLICATIONS

Butson et al., "Current Steering to Control the Volume of Tissue Activated During Deep Brain Stimulation," Brain Stimulation 1, 2008, pp. 7-15.

(56) References Cited

OTHER PUBLICATIONS

Butson et al., "Patient Specific Analysis of the volume of tissue activated during deep brain stimulation," NeuroImage, Academic Press, vol. 34, No. 2, Dec. 2, 2006, pp. 661-670.
Butson et al., "Role of Electrode Design on the Volume of Tissue Activated During Deep Brain Stimulation," Journal of Neural Engineering, Mar. 1, 2006, vol. 3, No. 1, pp. 1-8.
Cover, T.M. et al., "Elements of information theory," (1991) John Wiley & Sons, New York, NY, pp. 1-542.
Dice, Lee R., "Measures of the Amount of Ecologic Association Between Species," Ecology 26(3) (1945), pp. 297-302. doi:10.2307/1932409, http://jstor.org/stable/1932409.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
European Patent Office, International Search Report in International Application No. PCT/US2012/053344, dated Nov. 26, 2012, 8 pages.
European Patent Office, International Search Report and the Written Opinion of the International Searching Authority in International Application No. PCT/US2012/050175, dated Oct. 26, 2012, 15 pages.
European Patent Office, International Search Report in International Application No. PCT/US2012/050181, dated Jan. 3, 2013, 7 pages.
Euopean Patent Office, International Search Report and the Written Opinion in International Application No. PCT/US2012/050170, dated Oct. 5, 2012, 15 pages.
European Patent Office, International Search Report in International Application No. PCT/US09/03017, dated Aug. 3, 2009, 7 pages.
European Patent Office, International Search Report in International Application No. PCT/US09/03038, dated Oct. 8, 2009, 9 pages.
European Patent Office, International Search Report in International Application No. PCT/US09/03040, dated Aug. 13, 2009, 7 pages.
European Patent Office, International Search Report in International Application No. PCT/US09/03049, dated Jan. 26, 2010, 8 pages.
European Patent Office, partial International Search Report in International Application No. PCT/US2012/030701, dated Feb. 15, 2013, 7 pages.
European Patent Office, partial International Search Report in International Application No. PCT/US2012/030705, dated Mar. 6, 2013, 7 pages.
European Patent Office, International Search Report and Written Opinion in International Application No. PCT/US2012/030700, dated Feb. 27, 2013, 9 pages.
European Patent Office, International Search report and Written Opinion in PCT application No. PCT/US12/050174, dated Mar. 6, 2013, 20 pages.
European Patent Office, International Search Report and Written Opinion in International Application No. PCT/US2012/050187, dated Feb. 27, 2013, 9 pages.
European Patent Office, International Search Report in International Application No. PCT/US09/03041, dated Aug. 20, 2009, 7 pages.
Hubert, Lawrence et al., "Comparing partitions," Journal of Classification 2(1) (1985), pp. 193-218, doi:10.1007/BF01908075.
Izad, Olivier, "Computationally Efficient Method in Predicating Axonal Excitation," Dissertation for Masters Degree, Department of Biomedical Engineering, Case Western Reserve University, May 2009, 144 pages.
Jaccard, Paul, "Étude comparative de la distribution florale dans une portion odes Aples et des Jura," Bulletin de la Société Vaudoise des Sciences Naturelles (1901), vol. 37, pp. 547-579.
Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Liliane Ramus et al, "Assessing selection methods in the context of multi-atlas based segmentation," Biomedical Imaging: From Nano to Macro, 2010 IEEE International Symposium, Apr. 14, 2010, pp. 1321-1324.
Lotjonen J.M.P. et al, "Fast and robust multi-atlas segmentation of brain magnetic resonance images," NeuroImage, Academic Press, vol. 49, No. 3, Feb. 1, 2010, pp. 2352-2365.
Meila, Marina, "Comparing Clusterings by the Variation of Information," Learning Theory and Kernel Machines (2003), pp. 173-187.
Miocinovic et al., "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Olivier Commowick et al., "Using Frankenstein's Creature Paradigm to Build a Patient Specific Atlas," Sep. 20, 2009, Medical Image Computing and Computer-Assisted Intervention, pp. 993-1000.
Rand, W.M., "Objective criteria for the evaluation of clustering methods," Journal of the American Statistical Association (American Statistical Association) 66 (336) (1971), pp. 846-850, doi:10.2307/2284239, http://jstor.org/stable/2284239.
Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
Schmidt et al., "Sketching and Composing Widgets for 3D Manipulation," Eurographics, Apr. 2008, vol. 27, No. 2, pp. 301-310.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.

* cited by examiner

100

```
┌─────────────────────────────────────────────────────┐
│ Apply a plurality of stimulus combinations to each patient │
│                        110                          │
└─────────────────────────────────────────────────────┘
                          │
                          ▼
┌─────────────────────────────────────────────────────┐
│ Evaluate efficacy of each combination to generate a │
│    behavioral score set for each combination        │
│                        112                          │
└─────────────────────────────────────────────────────┘
                          │
                          ▼
┌─────────────────────────────────────────────────────┐
│      Register patient, generate patient record      │
│                        114                          │
└─────────────────────────────────────────────────────┘
                          │
                          ▼
┌─────────────────────────────────────────────────────┐
│  For each combination, calculate an electric field map │
│                        116                          │
└─────────────────────────────────────────────────────┘
```

Receive score criteria as input
210

Extract stimulation parameter combinations and corresponding field maps for which the scores satisfy the score criteria
212

Generate a weighted field map as a function of the field map values and the score values respectively associated with the field maps of each similarly-situated patient
214

Determine which stimulation parameter combinations result in a field map that most closely matches the target field map and select those settings as the optimal combination
216

```
For each similarly-situated patient,
perform series expansion of each field map to generate a
coefficient set for each map
310
```

```
Perform regression analysis using the coefficient values as
independent variables and the corresponding scores as
dependent variables
312
```

```
Apply score criteria to the results of regression analysis to
determine which coefficient values most closely relate to the
score criteria (generate target coefficient sets)
314
```

```
Compare the coefficient sets of the current patient and
determine which coefficient set most closely matches one of
the target coefficient sets and select the combination
associated with the matching coefficient set as the optimal
combination
316
```

Fig. 4

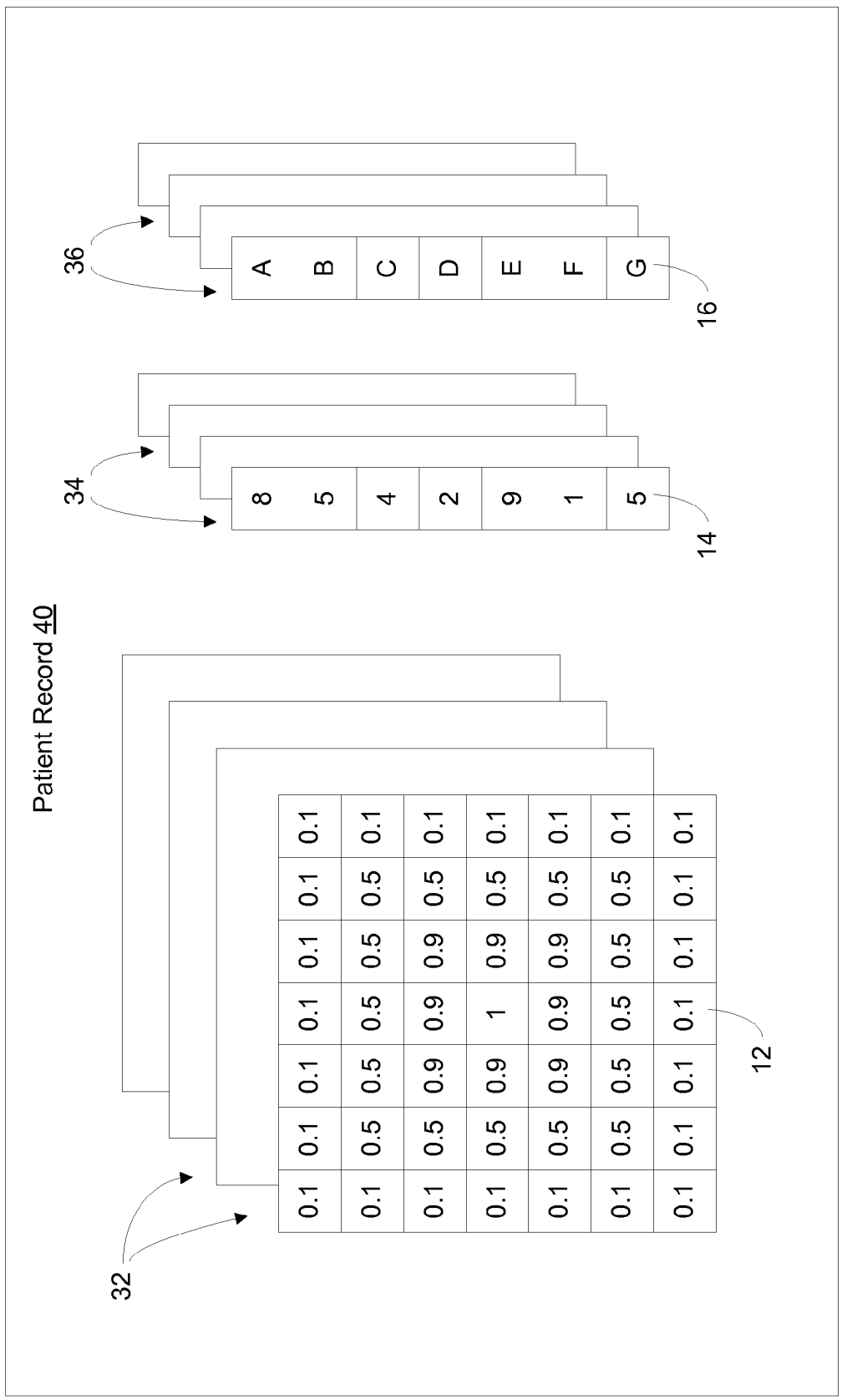

METHODS AND SYSTEM FOR TARGETED BRAIN STIMULATION USING ELECTRICAL PARAMETER MAPS

CROSS REFERENCE TO RELATED APPLICATION

The present application claims priority to U.S. provisional application Ser. No. 61/530,142 filed on Sep. 1, 2011, the disclosure of which is incorporated herein by reference in its entirety.

FIELD OF THE INVENTION

In general, the present invention relates to methods and systems for electrical stimulation of an anatomical region of the body, such as the nervous system. More particularly, the present invention relates to methods and systems for determining target stimulation parameter settings for patient stimulation.

BACKGROUND INFORMATION

Electrical stimulation of the nervous system, including the brain and spinal cord, exists as a potentially effective, but also risky treatment option for various medical conditions such as pain, epilepsy, dystonia, Parkinson's disease and depression. In addition to potential health complications arising from surgical implantation of stimulation hardware (e.g., an implanted pulse generator (IPG) and a stimulation electrode), there exists the problem of determining what type of stimulation each patient should receive. Since the brain anatomy and electrode placement is different between patients, there is no standard course of treatment that is universally applicable to all patients. For example, the same stimulation parameters (e.g., pulse width, pulse duration, amplitude, polarity, etc.) tend to produce different results for different patients.

Additionally, stimulation hardware is advancing so as to provide healthcare professionals with an ever-growing number of stimulation options. For example, IPGs are currently available which are capable of simultaneously producing outputs of different amplitude, e.g., for different electrodes and different leadwires. Electrode leads have also advanced to include multiple contacts that, when combined with the IPGs, allow individual contacts to be stimulated in different ways, whereas older-generation leads required the same stimulation signal to be applied to all contacts in a given lead. Accordingly, there is a need for tools that allow for accurate and efficient determinations of what combinations of stimulation parameters are required for a given patient.

One known approach to predicting stimulation effects involves the creation of brain stimulation field models (SFMs), also referred to as volumes of activation (VOAs) or volumes of tissue activated (VTAs). For example, U.S. Pat. No. 7,346,382 to McIntyre et al., the contents of which is incorporated herein by reference, describes the use of axon or neuron models which may be used to calculate an estimated VOA that results from a given stimulation parameter combination, and describes a target VOA to which such estimated VOAs may be compared.

Predicting stimulation effects by modeling estimated VOAs using axon or neuron models can involve a large processor load, and can require assumptions about the biophysics of the brain. For instance, it may require assumptions about the distribution density or the triggering thresholds of axons in a particular brain region.

BRIEF DESCRIPTION OF THE DRAWINGS

FIG. 1 is a flowchart that shows a method for associating behavioral scores with electric field maps according to an example embodiment of the present invention.

FIG. 3A is a flowchart that shows a method for determining an optimal stimulation parameter combination according to an example embodiment of the present invention.

FIG. 4 is a flowchart that shows a second method for determining an optimal stimulation parameter combination according to an example embodiment of the present invention.

FIG. 5A shows an exemplary patient data record generated according to the method of FIG. 4.

SUMMARY

Figure 2:
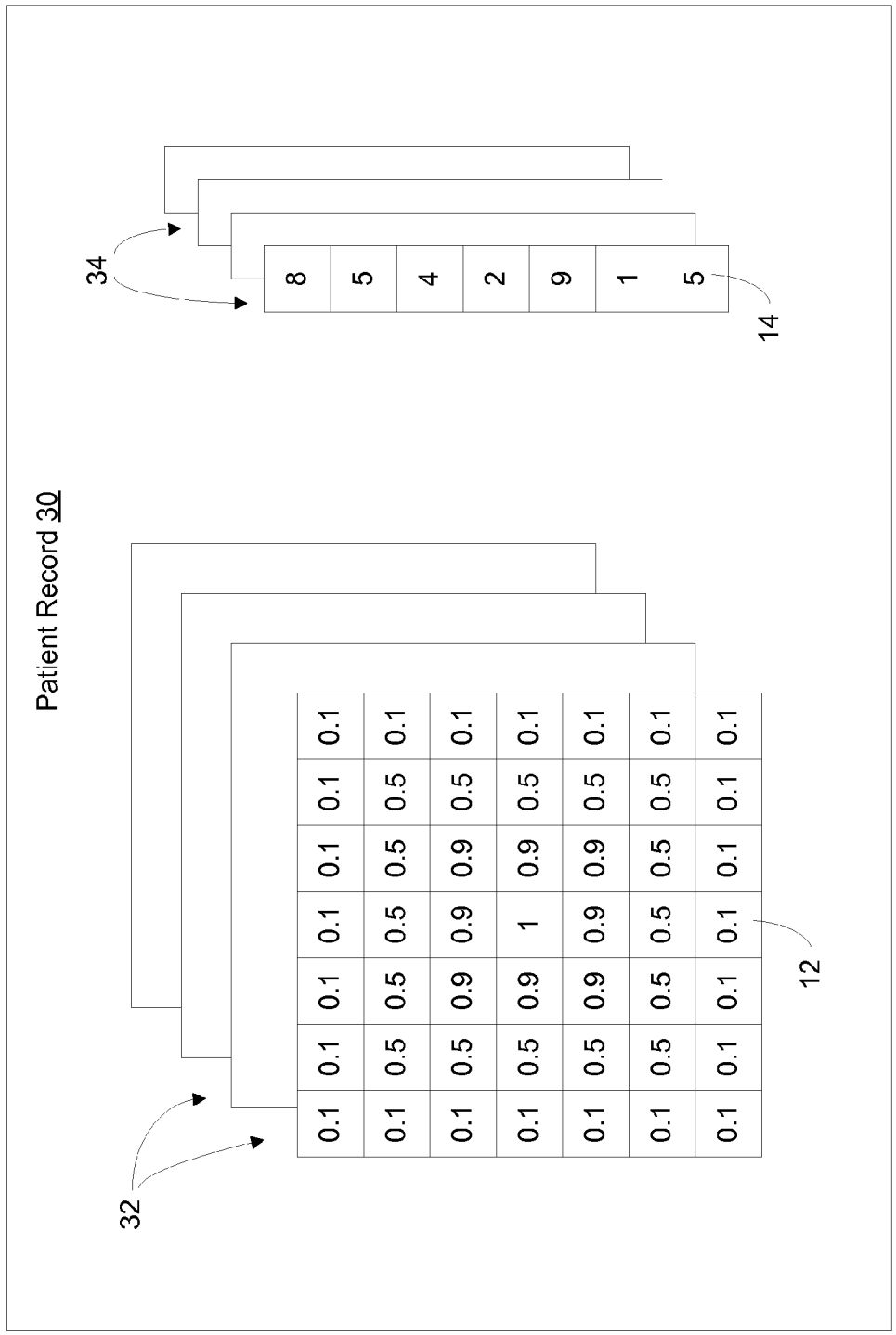
FIG. 2 shows an exemplary patient data record generated according to the method of FIG. 1.

Example embodiments of the present invention relate to methods and corresponding system(s) for selecting optimal neural stimulation parameters using electrical parameter maps, e.g., by applying a threshold to a score map or a map obtained by weighting electric field values by scores. The neural stimulation includes stimulation of the brain, spinal cord, central and peripheral nerves. In a preferred embodiment, the methods and systems apply to brain stimulation. According to example embodiments, the target stimulation parameters may be determined without reference to a target VOA.

According to example embodiments, patients are registered into a common database to form a patient registry. Various stimulation parameter combinations for a patient population are computer-simulated to calculate electric field maps containing potential difference values, i.e., voltages. With respect to calculation of electric field maps, see, e.g., U.S. patent application Ser. No. 12/454,330, filed May 15, 2009 ("the '330 application"), which issued as U.S. Pat. No. 8,831,731, U.S. patent application Ser. No. 12/454,312, filed May 15, 2009 ("the '312 application"), which issued as U.S. Pat. No. 8,326,433, U.S. patent application Ser. No. 12/454,340, filed May 15, 2009 ("the '340 application"), which published as U.S. Pat. App. Pub. No. 2009/0287272, U.S. patent application Ser. No. 12/454,343, filed May 15, 2009 ("the '343 application"), which published as U.S. Pat. App. Pub. No. 2009/0287273, and U.S. patent application Ser. No. 12/454,314, filed May 15, 2009 ("the '314 application"), which issued as U.S. Pat. No. 8,849,632, the content of each of which is hereby incorporated herein by reference in its entirety. The field maps may be stored in association with corresponding behavioral score sets. The behavioral scores represent the actual effects produced by testing specific stimulation parameter combinations on the patient population, and are used in conjunction with the field maps as a basis for selecting an appropriate stimulation parameter combination for use with a new patient. Thus, one aspect of the present invention relates to the generation of field maps and score sets of a patient population, where the field maps and score sets are used by a system for determining target stimulation parameter settings for a new patient.

According to example embodiments of the present invention, a system and method may determine optimal stimulation parameter combinations that are likely to produce behavioral scores matching user-specified score criteria or predetermined score criteria with which the system is programmed. According to an example embodiment, optimal stimulation parameter combinations may be determined by extracting a set of stimulation settings and corresponding field maps, which are associated with scores that satisfy the score criteria. Each extracted field map is then weighted on a voxel-by-voxel basis by its respective score to generate a respective weighted field map. Those weighted field maps are then averaged over multiple patient datasets to compute a weighted average field map. Finally, this weighted average field map is compared with an individual patient's field map for each possible stimulation parameter combination for the patient. The parameter combination for which the patient's field map has the greatest agreement and least disagreement with the weighted average field map is selected as the optimal combination.

As an alternative to comparing against the weighted average field map, the current patient's field maps, corresponding to various parameter combinations, may be compared with field maps of patients with known scores. Then each of the current patient's field maps may be assigned the same score as that of a closest matching field map from the patient population. The parameter combination corresponding to the patient's field map having the best score is then selected as the optimal combination.

According to an alternative example embodiment of the present invention, optimal stimulation parameter combinations may be determined by applying a series expansion (e.g., a Fourier-Bessel expansion) to the field maps of the patient population in order to represent each of the field maps as a sum of mathematical functions. Each field map may then be represented by a set of coefficients associated with the mathematical functions, e.g., where each coefficient indicates a degree to which a respective one of the functions characterizes the respective field map. The coefficient sets are analyzed with respect to their corresponding scores using regression or likelihood model analysis to generate a model relating the coefficient sets to behavioral score sets. The resulting model is used to generate a target coefficient set made up of coefficient values that represent a field map that is likely to produce behavioral scores meeting a score criterion. The target coefficient set is compared to the current patient's own coefficient sets. The stimulation parameter combination associated with the best matching one of the current patient's coefficient sets is then selected as the optimal combination. Alternatively, the resulting model is used to calculate a set of predicted scores for each of the current patient's coefficient sets. The parameter combination associated with the coefficient set having the score set that best meets the score criteria is then selected as the optimal combination.

DETAILED DESCRIPTION

Patient Registration: Generation of Field Maps and Score Maps

FIG. 1 shows an exemplary method 100 for associating behavioral scores with field maps according to the present invention. The method 100 involves the use of stimulation data from a plurality of patients in a patient population. At step 110, a plurality of stimulation parameter combinations may be applied to patients of the patient population. One or more of such stimulations for a patient of the patient population may occur soon after stimulation hardware has been implanted into the patient, since various stimulation parameter combinations are typically tested to determine (by trial-and-error) at least one efficacious stimulation parameter combination before discharging the patient from a medical institution where the implantation occurred.

At step 112, the efficacy of each stimulation parameter combination is evaluated to generate a behavioral score set for each combination. Each score corresponds to a behavior associated with an improvement, e.g., mental alertness, or a side-effect, e.g., involuntary muscle contraction. The scores may be scaled, with higher scores indicating a greater presence of the associated behavior. For example, each score may be an integer number from one to ten. The scores may be specified based on the subjective responses of the patients and/or based on observations made by medical personnel. In one embodiment, Unified Parkinson's Disease Rating Scale (UPDRS) scores may be used.

At step 114, each patient is registered into a common patient registry database. A patient record is created to store personal information and medical records, such as pre-op or post-op brain images. A registration procedure may also involve adjusting a reference brain model, i.e., an atlas having defined brain sections, to fit the brain anatomy of the individual patient. The reference model can be morphed, e.g., stretched or transformed, to match a CT, MRI, or an image of another imaging modality, resulting in a patient atlas. Typically, the patient atlas includes an indication of where a lead is implanted, e.g., the locations of the lead tip and electrodes.

At step 116, an electric field map is calculated for each stimulation parameter combination of the patient of the patient population. The electric field map may include a three-dimensional plot of voltage potentials that exists in a plurality of locations around the electrodes. The voltage potentials may be simulated voltages arising from the application of the stimulation parameter combination. For example, a monopolar electrode may generate a spherical voltage pattern with the highest voltage values located at the center, i.e., the electrode, and with the voltages decreasing with radial distance. Such a pattern is shown in an exemplary field map 32 in FIG. 2. The field map 32 may include a voxel matrix, with each voxel 12 being assigned a single voltage value. For illustrative purposes, the field maps 32 are shown as two-dimensional matrices. However, it will be understood that each field map 32 is actually three-dimensional, i.e., a 3-D matrix of voxels.

FIG. 2 also shows an exemplary patient data record 30 generated during the registration process. Each record 30 includes one or more field maps 32 generated according to step 116. Additionally, each record 30 includes one or more corresponding behavioral score sets 34 that include individual scores 14, where different scores of a single set pertain to different measured categories with respect to a single respective one of the field maps. The number of scores 14 may vary depending on any number of factors, such as the nature and complexity of the patient's medical condition, and procedural differences in the recording practices of different medical institutions. Each behavioral score set 34 is associatively linked in the database to its corresponding field map 32, which is in turn linked in the database to the specific stimulation parameter combination that generated the field map 32.

Exemplary methods 200/300/400 for generating optimal stimulation parameter combinations based on the database of patient population information will now be described. The methods 200/300/400 involve analyzing the field maps 32 and the behavioral score sets 34 against user-specified or predetermined system-programmed score criteria to determine an optimal stimulation parameter combination. Thus, the methods 200/300/400 provide an alternative to VOA-based stimulation parameter selection.

Weighted Average of Field Values

FIG. 3A is a flowchart that shows the method 200 for determining an optimal stimulation parameter combination according to an example embodiment of the present invention. At step 210, one or more user-specified score criteria are received as input. The user may be a medical technician or a physician who selects a set of behaviors and inputs, as the score criteria, a threshold score for each selected behavior. Alternatively, scores may be on an overall clinical profile basis, e.g., where the system is configured to determine which scored behaviors are relevant to an input clinical profile, e.g., which behaviors are relevant to a Parkinson's disease (PD) patient, and which score thresholds to apply. In this manner, the user can specify the types of behaviors that the stimulation parameter combination should provide and/or avoid, along with the degree to which the patient should exhibit the specified behaviors in response to the optimal stimulation parameter combination, i.e., a score or score range. To illustrate, the user may specify pain reduction above a certain level and headache below a certain level.

At 212 a thresholding procedure is performed by extracting stimulation parameter combinations and corresponding field maps for those scores that satisfy the score criteria. For each patient in the patient population who exhibits a score satisfying one of the score criteria, the stimulation parameter combinations that produced the satisfactory score are extracted, along with the corresponding field map generated by those combinations. In this manner, a set of field maps/parameter combinations may be extracted for each relevant score category.

It is noted that the scores may be representative of a degree of improvement or degradation with respect to the rated category, rather than an absolute rating of the category. Where the scores are representative of absolute values, the system may calculate relative scores representative of the degree of improvement or degradation by comparison to prior scores. Scores representative of a degree of improvement and/or degradation may be used, as absolute ratings are less informative of the effect on the rated category by the applied stimulation.

Step 214 may be performed on the extracted field maps of those patients of the patient population who are similarly-situated to the current patient. For example, patients may be considered similarly-situated when they share the same medical condition, physical characteristics and/or identical implant locations. The behavioral responses of similarly-situated patients are generally more predictive of the current patient's response to similar stimuli, whereas the responses of the overall patient population are generally less predictive.

At step 214, the field map values of the extracted field maps are weighted by the scores of each respective extracted field map. Weighting may be performed by calculating, for each voxel, the product (V×S) for all values of the respective voxel in the considered field maps, where V is the voltage value for a particular voxel and S is the score associated with the field map 32 in which the voxel is located. Weighted extracted field maps belonging to the same score category are then averaged together (i.e., summed and then divided by the total number of field maps summed) to generate a single weighted average field map 42 for each relevant score category.

Figure 3B:
FIG. 3B shows example embodiments of a pair of extracted field maps and a corresponding weighted average field map.

Alternatively, a single weighted average field map 42 may be generated that is representative of all relevant score categories. For example, the system may determine for each considered field a single score representative of the combination of scores of the different score categories. Moreover, based on the relevant clinical profile, different weights may be applied to the scores of the different categories to obtain the single representative score. For example, for a certain clinical profile, it may be determined that score category 1 is most important and score category 2 is less important, and therefore the score of score category 1 may be more highly weighted than the score of score category 2. However, if the current patient has a different clinical profile, score category 2 may be considered more important, and therefore more highly weighted, than score category 1. The single weighted average score may be used to weight each respective extracted field map before performing averaging to generate the single weighted average field map 42 as a target field map. FIG. 3B shows example embodiments of a pair of extracted field maps 44/45 and a corresponding weighted average field map 42.

At step 216, the system may determine which stimulation parameter combinations result in a field map that most closely matches the weighted average field map 42. Optionally, the weighted average field map may be displayed to the user as a visual approximation of the influence of each voxel on behavioral improvement and/or side-effect avoidance and the user may scroll through parameter combinations to obtain a field map that is maximally concordant with voxels with the greatest influence on behavioral improvement and maximally discordant with the voxels with the least influence on behavioral improvement or the largest influence on side-effects.

As an alternative to comparing against the weighted average field map, each of the current patient's field maps may be compared with field maps of patients with known scores. Then each of the current patient's field maps may be assigned the same score as that of a closest matching field map from the patient population. The stimulation parameter combination corresponding to the patient's field map having the best score is then selected as the optimal combination.

Series Expansion of Field Maps with Comparison of Coefficient Sets

FIG. 4 is a flowchart that shows the method 300 for determining an optimal stimulation parameter combination according to an example embodiment of the present invention. The methods 300 and 400 are more computationally expensive compared to the method 200, but provide more accurate representations of the relationship between the stimulation parameter combinations, their corresponding field maps, and the score sets.

At step 310, a series expansion is performed on each of the field maps of each similarly-situated patient. Any series expansion may be used. In one embodiment, a Fourier-Bessel series expansion may be performed to derive a mathematical representation for each field map, i.e., a sum of products of real and complex exponentials and Bessel functions, where each product has associated with it a coefficient. The complex exponentials represent the time-varying part of the field map and the real exponentials and Bessel functions represent its spatial variation. Alternatively, other special functions may be used in combination with complex exponentials. These special functions may be selected from any number of known basis function sets, including spherical harmonics functions.

In an alternative embodiment, a Fourier-Spherical Harmonics expansion may be performed, using complex exponential functions to represent a time-varying component of the field map values and using spherical harmonics functions to represent a spatially-varying component of the field map values.

As mentioned above, each term in the series expansion is accompanied by a coefficient. The set of coefficients representing a respective one of the field maps can be used as a surrogate for the actual voltage values of the respective field map. The coefficients provide a more convenient way to analyze the field maps, which are highly dimensional; each field map is a three-dimensional matrix of voltages at each of a very large number of voxels, whereas only a few coefficients are significantly different from zero and therefore provide a compressed representation of the data.

FIG. 5A shows an exemplary patient data record 40, which includes the field maps 32 and the behavioral score sets 34 previously described in connection with the patient record 30 of FIG. 2. Additionally, the patient record 40 includes one or more coefficient sets 36 having coefficient values 16. Shown symbolically using the letters A through G, the coefficient values 16 may be any number, e.g., a real number or a complex number having real and imaginary components.

At step 312, a regression or likelihood analysis is performed, in which the coefficient values 16 are the independent variables and the corresponding scores 14 are the dependent variables. Regression is sometimes defined as the task of finding a function relating independent and dependent variables. The term "likelihood" is more specific and used when the dependent variables are related probabilistically to the independent variables. The terms "regression" and "likelihood" are used interchangeably herein to refer to the same concept, i.e., the more specific form of regression in which dependent and independent variables are probabilistically related.

Figure 5B:
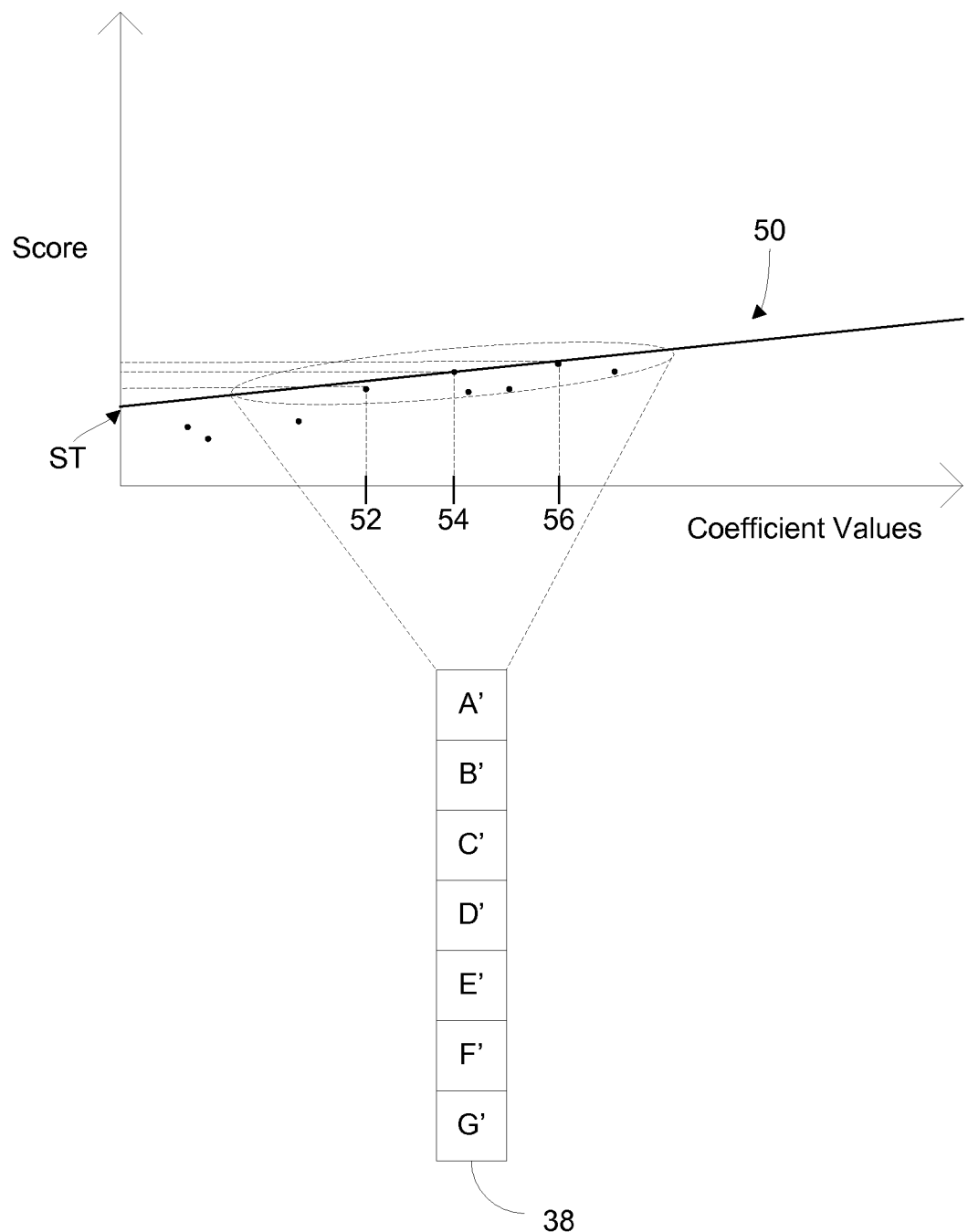
FIG. 5B shows an exemplary target coefficient set according to an example embodiment of the present invention.

In one embodiment, the analysis may be performed by building a generalized additive model. Alternatively a generalized linear model (not to be confused with a general linear model) may be built. Other types of models may also be implemented. After inputting the coefficient sets 36 and the score sets 34 into a regression analysis algorithm, a probabilistic distribution is output. As shown in FIG. 5B, the distribution may be visually displayed as a scatter plot in which coefficient values form the x-axis and score values form the y-axis. A separate plot may be provided for each behavior category, i.e., a uni-variate regression model may be built for individual behaviors, e.g., a single model for each behavior of the user-specified score criteria. Alternatively, a multi-variate model may be built to indicate the relationship between the coefficient values and a plurality of behaviors. For instance, the multi-variate model may indicate how the coefficient values relate to the behaviors of the user-specified score criteria.

At step 314, the results of the regression analysis may be applied to the score criteria to determine which coefficient values are most closely related to the score criteria. For example, if the score criteria require that tremor be below a certain value, at least one coefficient value set that will produce tremor below the required value is output. Any number of coefficient value sets that meet the score criteria may be output in this manner. To illustrate, in FIG. 5B, if the score criteria includes a minimum score of ST, a set of coefficient values that generate score values equal to or above ST are selected to form a target coefficient set 38.

At step 316, the target coefficient sets 38 may each be compared to the coefficient sets of the current patient to determine which of the current patient's existing coefficient sets most closely matches any one of the target coefficient sets 38. The stimulation parameter combination associated with a best matching one of the current patient's coefficient sets is then selected as the optimal combination. For example, the system may estimate voltage fields for various possible parameter combinations for the current patient, convert such estimated voltage fields to coefficient sets, and compare each such coefficient set to the coefficient sets determined by the regression analysis as meeting the score criteria.

Series Expansion of Field Maps with Comparison of Predicted Scores

Figure 6:
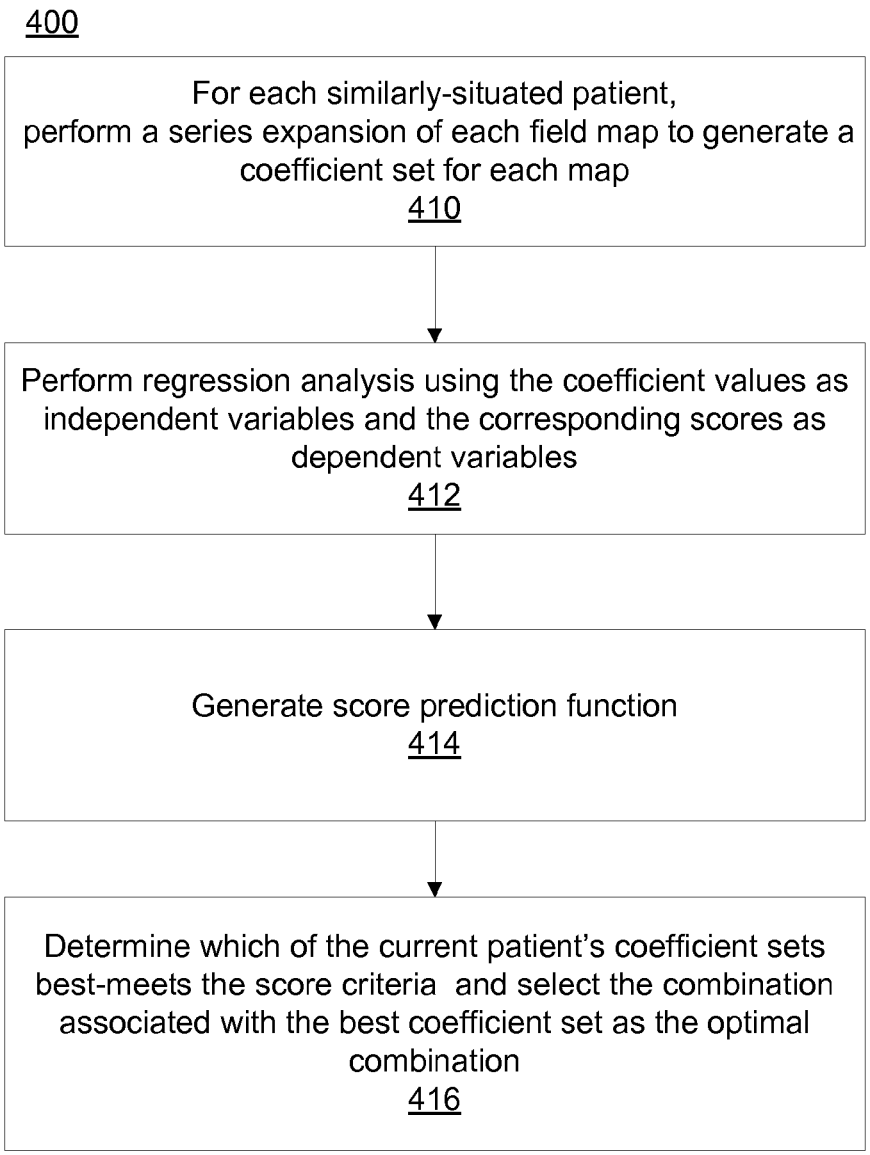
FIG. 6 is a flowchart that shows a third method for determining an optimal stimulation parameter combination according to an example embodiment of the present invention.

FIG. 6 is a flowchart that shows a method 400 for determining an optimal stimulation parameter combination according to an example embodiment of the present invention. The method 400 may include steps 410/412, which are analogous to steps 310/312 of the method 300.

The regression analysis described above in connection with the method 300 may also be used to predict a set of scores for each of the current patient's coefficient sets. In one embodiment, the analysis may model each predicted score set as a linear function. For example, in FIG. 5B, a line 50 may be interpolated using data points 52/54/56 so that the predicted score for any coefficient having an x-axis value is the corresponding y-axis value along the line 50. In an alternative embodiment, the predicted score set may be modeled as a distribution function. Instead of interpolating a line through the data points 52/54/56, the method 400 would model the data points as a probability distribution so that, for a given x-axis value, the predicted score would be the corresponding y-axis value according to the probability distribution. Therefore, as an alternative to comparing the current patient's coefficient sets against the target coefficient sets 38, scores may be predicted for each of the current patient's coefficient sets and directly compared to the score criteria.

At step 414, a score prediction function may be generated, e.g., by fitting a linear function that maps coefficient values to score values, or by generating a probability distribution function that characterizes the distribution that resulted from the regression analysis.

At step 416, it may be determined which of the current patient's coefficient sets best meets the score criteria. A score set may be calculated for each of the current patient's coefficient sets based on the score prediction function. The coefficient set having the most number of coefficient values that satisfy the score criteria within a certain tolerance level (e.g., predicted scores within a predetermined range of the score criteria are acceptable even if below a specified score value) may then be determined as being the best. The stimulation parameter combination associated with the best coefficient set is then selected as the optimal combination.

System Overview

Figure 7:
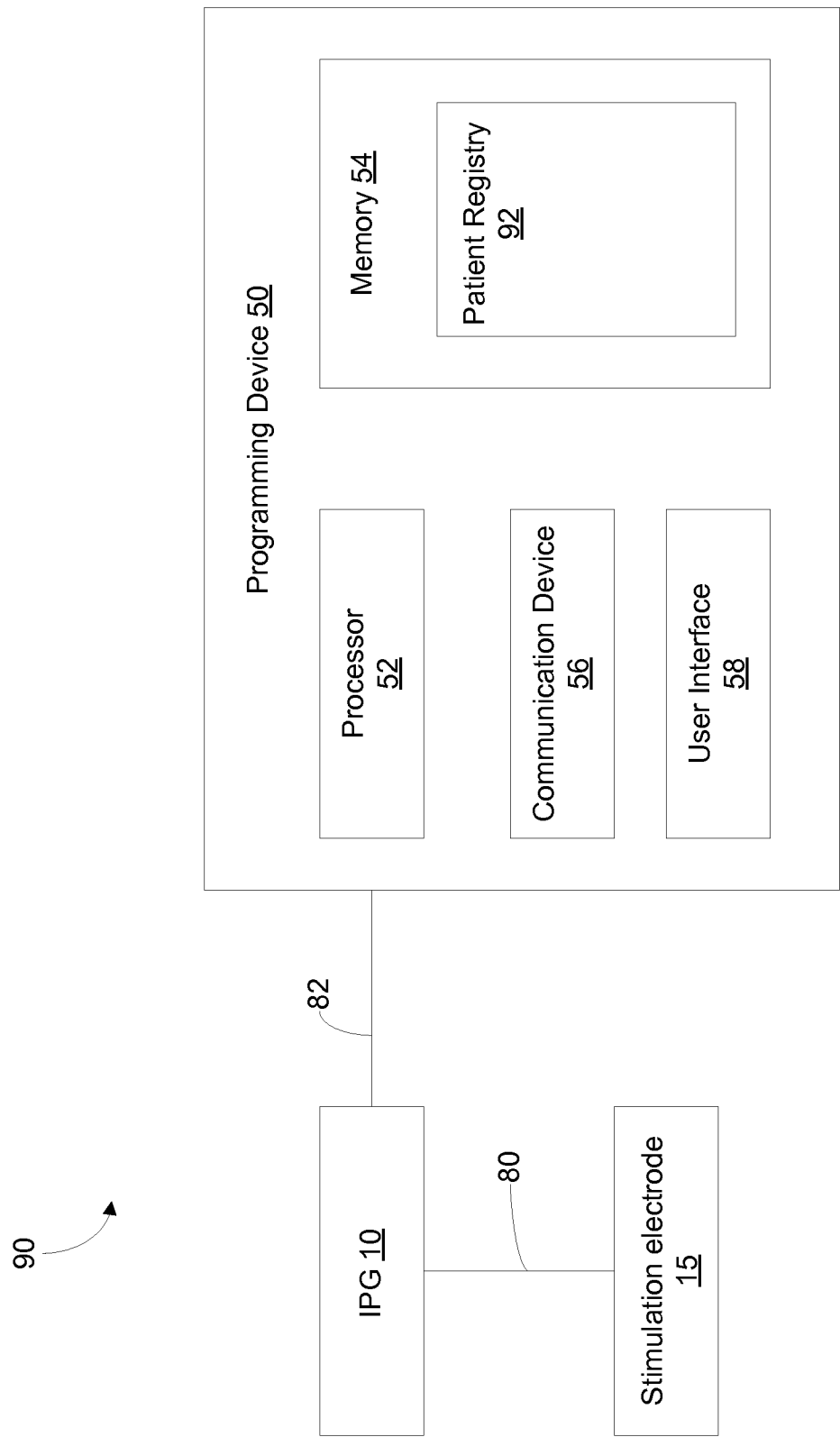
FIG. 7 is a block diagram that shows a system for brain stimulation according to an example embodiment of the present invention.

FIG. 7 is a block diagram that shows a system 90 for brain stimulation according to an example embodiment of the present invention. The system 90 may include an IPG 10, a stimulation electrode 15 attached to the IPG 10, and a programming device 50 that controls the electrode 15 via the IPG 10. For example, the programming device 50 may program the IPG 10 by transmitting the optimal stimulation parameter combination for storage in a memory of the IPG 10.

The programming device 50 may include a processor 52, a communication device 56, a user interface 58, and a memory device 54. The processor 52 may execute instructions in accordance with any of the methods described above. The communication device 56 may receive patient data, e.g., a data file sent from the IPG 10 or a remote computer. Such data may be of the current patient for whom target stimulation parameter combinations are calculated and/or of the patient population. The user interface 58 may include an input device, e.g., a mouse or a keyboard, as well as an output device such as a display screen. The memory device 54 may store a patient registry 92, containing a patient record 30 for each registered patient. It is noted that information obtained concerning the current patient may be used to update the patient population information used subsequently for determining target parameter combinations for the current patient or another patient. In an example embodiment, the patient registry 92 database may be stored at a central location, accessible via a network by a plurality of devices running programming modules for selecting target stimulation parameters.

The various methods described herein may be practiced, each alone, or in various combinations.

An example embodiment of the present invention is directed to one or more processors, which may be implemented using any conventional processing circuit and device or combination thereof, e.g., a Central Processing Unit (CPU) of a Personal Computer (PC) or other workstation processor, to execute code provided, e.g., on a hardware computer-readable medium including any conventional memory device, to perform any of the methods described herein, alone or in combination. The memory device may include any conventional permanent and/or temporary memory circuits or combination thereof, a non-exhaustive list of which includes Random Access Memory (RAM), Read Only Memory (ROM), Compact Disks (CD), Digital Versatile Disk (DVD), and magnetic tape.

An example embodiment of the present invention is directed to a hardware computer-readable medium, e.g., as described above, having stored thereon instructions executable by a processor to perform the methods described herein.

An example embodiment of the present invention is directed to a method, e.g., of a hardware component or machine, of transmitting instructions executable by a processor to perform the methods described herein.

Example embodiments of the present invention are directed to one or more of the above-described methods, e.g., computer-implemented methods, alone or in combination.

The above description is intended to be illustrative, and not restrictive. Those skilled in the art can appreciate from the foregoing description that the present invention may be implemented in a variety of forms, and that the various embodiments may be implemented alone or in combination. Therefore, while the embodiments of the present invention have been described in connection with particular examples thereof, the true scope of the embodiments and/or methods of the present invention should not be so limited since other modifications will become apparent to the skilled practitioner upon a study of the drawings, specification, and appendices. For example, while the system and methods have been described with respect to field maps containing potential difference values (which are first difference values), alternative embodiments may utilize second difference values calculated from the potential difference values. For example, embodiments may utilize, as field map values, the magnitude of the second derivative of the potential difference values taken, for example, along directions of the fiber pathways in a region of interest, i.e., the region corresponding to the anatomical location of each field map. The direction of the fiber pathways can be estimated based on the patient atlas and information about the directionality of fiber pathways in a standard reference brain.

Example embodiments of the present invention have been described in connection with electric field maps. However, it will be understood that any electrical parameter may be used, including, but not limited to, current density and activating functions. Each of these alternative parameters may be used to form maps in place of the field map in the various methods and systems described above. For example, a weighted average of current density map values may be performed. Similarly, a series expansion of an activating function map may be performed.

Further, steps illustrated in the flowcharts may be omitted and/or certain step sequences may be altered, and, in certain instances multiple illustrated steps may be simultaneously performed.

What is claimed is:

1. A system for selecting optimal stimulation parameter settings for a current patient, comprising:
at least one computer processor configured to:
obtain a plurality of electrical parameter maps and corresponding score values from a plurality of patients including the current patient, each electrical parameter map corresponding to a one of the plurality of patients and representing different sets of one or more electrical stimulation parameters, wherein each of the score values is associated with one of the different sets of one or more electrical stimulation parameters and represents a behavior of the patient upon electrical stimulation using that set of one or more electrical stimulation parameters; and
process the electrical parameter maps and the score values to evaluate, based on a set of score criteria, potential parameter maps, including a potential parameter map that is different than all of the plurality of electrical parameter maps, associated with respective potential stimulation parameter settings.

2. The system of claim 1, wherein at least one of the potential parameter maps is calculated based on simulated stimulation parameter settings.

3. The system of claim 1, wherein each electrical parameter map is an electric field map that includes voxels containing voltage values.

4. The system of claim 1, wherein each electrical parameter map is an electric field map that includes voxels containing second differences of voltage values.

5. The system of claim 1, wherein each electrical parameter map is an electric field map that includes voxels containing second derivatives of voltage values, taken along estimated directions of fiber pathways in a brain region to which the field map corresponds.

6. The system of claim 1, wherein each electrical parameter map is a current density map that includes voxels containing current values.

7. The system of claim 1, wherein each electrical parameter map is an activating function map that includes voxels containing activating function values.

8. The system of claim 1, wherein the set of score criteria includes at least one user-input score criterion.

9. The system of claim 1, wherein the set of score criteria includes at least one score criterion that is predetermined based on a clinical profile of the current patient.

10. The system of claim 1, wherein the score values include, for each of at least a subset of the electric parameter maps, a plurality of score values, different ones of the plurality of score values corresponding to different behavior categories.

11. The system of claim 1, wherein only the electrical parameter maps of patients who are similarly-situated to the current patient are processed.

12. The system of claim 1, wherein the processing of the electrical parameter maps comprises:
thresholding the electrical parameter maps based on the score criteria to extract a set of parameter maps that meet the score criteria; and
generating a weighted average parameter map, as one of the potential parameter maps, as a function of parameter map values and respective score values corresponding to the extracted parameter maps that meet the score criteria.

13. The system of claim 12, wherein the optimal stimulation parameter settings are selected based on a determination that the optimal stimulation parameter settings will generate a potential parameter map that best matches the weighted average parameter map compared to potential parameter maps corresponding to other tested stimulation parameter settings.

14. The system of claim 12, wherein each value of the weighted average parameter map is generated by averaging a product V ×S for all of the extracted parameter maps, where V is a corresponding parameter map value and S is a respective derived score value derived from the score values corresponding to the respective extracted parameter map from which the corresponding parameter map value V is obtained.

15. The system of claim 14, wherein the derived score value S is a single score value selected from the score values of the respective extracted parameter map from which the corresponding parameter map value V is obtained.

16. The system of claim 14, wherein the derived score value S is derived from a combination of the score values of the respective extracted parameter map from which the corresponding parameter map value V is obtained.

17. The system of claim 1. each of the plurality of electrical parameter maps is a spatial distribution of electrical values, which the processor associated with a respective set of stimulation parameter settings, the processing of the electrical parameter maps includes analyzing a correspondence between the plurality of spatial distributions of electrical values to their corresponding score values, and the processor is configured to select, based on the set of score criteria, stimulation parameter settings estimated to produce an electrical distribution which the analysis indicates would satisfy the score criteria.

18. The system of claim 1, wherein the processing of the electrical parameter map comprises:
for each of at least a subset of the electrical parameter maps, performing a series expansion to generate for each electrical parameter map a set of expansion terms, each expansion term including a mathematical function and a corresponding coefficient value ;
performing a regression analysis to determine a probabilistic relationship between coefficient values and score values specified by at least one of the score criteria; and
based on the probabilistic relationship, determining which of a plurality of coefficient sets corresponding to the electrical parameter maps of the current patient provides score values that best meets the score values specified by the at least one of the score criteria.

19. The system of claim 18, wherein the processing of the electrical parameter maps further comprises:
generating at least one target coefficient set by selecting coefficient values that most-closely relate to the score values specified by the at least one of the score criteria;
determining which of the plurality of coefficient sets of the current patient best matches at least one of the generated target coefficient sets; and
selecting settings associated with the matching coefficient set.

20. The system of claim 18, wherein the processing of the electrical parameter maps further comprises:
generating a score prediction function based on the probabilistic relationship;
using the score prediction function, calculating a set of predicted scores for each of the plurality of coefficient sets of the current patient;
determining which of a plurality of coefficient sets of the current patient has a predicted score set that best meets the score values specified by the at least one of the score criteria; and
selecting settings associated with the coefficient set that has the best meeting predicted score set.

21. The system of claim 18, wherein the series expansion is a Fourier-Bessel expansion and each coefficient value corresponds to a complex exponential function, a real exponential function and a Bessel function.

22. The system of claim 18, wherein the series expansion is a Fourier-Spherical Harmonics expansion and each coefficient value corresponds to a complex exponential function and a spherical harmonics function.

23. The system of claim 18, wherein each coefficient value indicates a degree to which a respective mathematical function reflects the electrical parameter map to which the set of coefficient values that contains the coefficient value corresponds.

24. The system of claim 18, wherein the regression analysis is performed using one of a generalized additive model or a generalized linear model.

25. The system of claim 18, wherein the regression analysis is performed using a uni-variate regression model for each score value specified by the at least one score criteria.

26. The system of claim 18, wherein the regression analysis is performed using a single, multi-variate regression model that indicates a relationship between the coefficient values and a plurality of score values specified by the at least one score criteria.

27. A computer-implemented method for selecting optimal stimulation parameter settings for a current patient, comprising:
obtaining, by a computer processor, a plurality of electrical parameter maps and corresponding score values from a plurality of patients including the current patient, each electrical parameter map corresponding to a one of the plurality of patients and representing different sets of one or more electrical stimulation parameters, wherein each of the score values is associated with one of the different sets of one or more electrical stimulation parameters and represents a behavior of the patient upon electrical stimulation using that set of one or more electrical stimulation parameters: and
processing, by the computer processor, the electrical parameter maps and the score values to evaluate, based on a set of score criteria, potential parameter maps, including a potential parameter map that is different than all of the plurality of electrical parameter maps, associated with respective potential stimulation parameter settings.

28. A non-transitory hardware-implemented computer-readable storage medium having stored thereon a series of instructions executable by a processor, the instructions which, when executed, cause the processor to perform a method for selecting optimal stimulation parameter settings for a current patient, the method comprising:

obtaining a plurality of electrical parameter maps and corresponding score values from a plurality of patients including the current patient, each electrical parameter map corresponding to a one of the plurality of patients and representing different sets of one or more electrical stimulation parameters, wherein each of the score values is associated with one of the different sets of one or more electrical stimulation parameters and represents a behavior of the patient upon electrical stimulation using, that set of one or more electrical stimulation parameters; and processing the electrical parameter maps and the score values to evaluate, based on a set of score criteria, potential parameter maps, including, a potential parameter map that is different than all of the plurality of electrical parameter maps, associated with respective potential stimulation parameter settings.

\* \* \* \* \*